United States Patent [19]
McKee et al.

[11] Patent Number: 5,994,399
[45] Date of Patent: *Nov. 30, 1999

[54] METHOD OF REGENERATING COLLAGEN-CONTAINING TISSUES WITH MISOPROSTOL

[76] Inventors: Rex N. McKee, 2368 Ridge Rd., Traer, Iowa 50675; Frank A. Wingrove, 1029 Sunrise Blvd., Waterloo, Iowa 50701

[ * ] Notice: This patent issued on a continued prosecution application filed under 37 CFR 1.53(d), and is subject to the twenty year patent term provisions of 35 U.S.C. 154(a)(2).

[21] Appl. No.: 08/825,244

[22] Filed: Mar. 27, 1997

[51] Int. Cl.⁶ .................................................. A61K 31/215
[52] U.S. Cl. ................................................................ 514/530
[58] Field of Search ............................................. 514/530

[56] References Cited

U.S. PATENT DOCUMENTS

| | | | |
|---|---|---|---|
| 3,965,143 | 6/1976 | Collins et al. | 260/468 D |
| 4,001,286 | 1/1977 | Bundy | 260/410.9 R |
| 4,009,282 | 2/1977 | Voorhees | 424/317 |
| 4,025,645 | 5/1977 | Jelenko, III | 424/312 |
| 4,113,882 | 9/1978 | Okazaki et al. | 424/317 |
| 4,132,738 | 1/1979 | Kluender et al. | 260/586 R |
| 4,181,725 | 1/1980 | Voorhees et al. | 424/258 |
| 4,185,100 | 1/1980 | Rovee et al. | 424/240 |
| 4,201,788 | 5/1980 | Voorhees et al. | 424/304 |
| 4,254,145 | 3/1981 | Birnbaum | 424/305 |
| 4,282,216 | 8/1981 | Rovee et al. | 424/240 |
| 4,353,896 | 10/1982 | Levy | 424/195 |
| 4,360,518 | 11/1982 | Rovee et al. | 424/240 |
| 4,459,310 | 7/1984 | Dajani | 424/305 |
| 4,473,565 | 9/1984 | Rovee et al. | 424/241 |
| 4,515,810 | 5/1985 | Chow et al. | 514/530 |
| 4,707,495 | 11/1987 | Rosenthale et al. | 514/530 |
| 4,840,968 | 6/1989 | Ohnishi | 514/530 |
| 4,889,845 | 12/1989 | Ritter et al. | 514/63 |
| 4,925,873 | 5/1990 | Friedhoff et al. | 514/469 |
| 5,015,481 | 5/1991 | Franz et al. | 424/494 |
| 5,145,686 | 9/1992 | Horrobin et al. | 424/677 |
| 5,167,952 | 12/1992 | McHugh | 424/49 |
| 5,310,759 | 5/1994 | Bockman | 514/573 |

OTHER PUBLICATIONS

Meguro, "Effect of prostaglandin on bovine synthesized macromolecules from succinate–1,4–14C," *Chemical Abstracts*, CA101(19):164424w, (1984).

Marks et al, "Local Infusion of Prostaglandin E–1 Stimulates Mandibular Bone Formation in–Vivo," *Biosis*, BA88:110 (1988).

*Primary Examiner*—Raymond Henley, III
*Attorney, Agent, or Firm*—McAndrews, Held & Malloy, Ltd.; Donald J. Pochopien; Andrew M. Everest

[57] ABSTRACT

A method of regenerating collagen-containing human tissues, especially bone, connective tissue, cartilage, facia, ligaments, tendons and other collagen-containing tissues of type I, II or III that have collagen as its organic constituent, and also epithelium, comprising topically administering to the damaged tissues a composition having an effective amount of misoprostol. Preferably, about 1 μg to about 1 mg misoprostol per gram of the composition is utilized in gel form.

6 Claims, No Drawings

METHOD OF REGENERATING COLLAGEN-CONTAINING TISSUES WITH MISOPROSTOL

CROSS-REFERENCE TO RELATED APPLICATIONS

STATEMENT REGARDING FEDERALLY SPONSERED RESEARCH OR DEVELOPMENT

BACKGROUND AND SUMMARY OF THE INVENTION

The present invention demonstrates methods of regenerating new collagen-containing tissue, e.g., bone, connective tissue, cartilage, facia, ligaments, tendons and other collagen tissue of type I, II, or III that have collagen as an organic constituent, and also epithelium. More specifically, this invention relates to a treatment comprising the use of misoprostol, an analog of prostaglandin $E_1$ for regenerating new collagen-containing tissues.

Loss of collagen can occur as a result of several mechanisms, e.g. genetic, enzyme degradation, or cell injury due to thermal, mechanical, chemical, and radiation (including UV light) traumas. This loss of collagen thins the skin, increases likelihood of injury and causes a delay in the healing response. At the present time no specific therapies exist to regenerate collagen after its breakdown, especially that associated with aging. In skin the attritional loss of collagen from breakdown and decreased synthesis of new collagen results in a thinning and the loss of structural integrity. The consequence of these changes is a looseness and wrinkling of the skin.

Recently, the discovery of natural products labeled as growth factors to promote growth and healing of connective and support tissues have been reported. These substances are usually proteins and appear to be ideal for inducing support and connective tissue repair, but in reality such factors are not practical as pharmaceutical agents. These proteins, like other proteins are not stable and break down upon storage. They also are not suitable for oral administration since they are digested and destroyed before entering the blood stream. Their administration as topical pharmaceutical agents is not possible. There then is only one route and that is parenteral but because they are proteins, they are recognized by the body as foreign. Thus, there is the constant danger of eliciting an immune response. This route does not necessarily target the right tissue and is more likely to affect many different cells throughout the body. The current invention uses topical application to areas of the body that require connective tissue repair and regeneration without oral or parenteral routes.

The present invention demonstrates new methods to regenerate connective and support tissues in humans and animals. These methods provide new treatment modalities useful in the treatment of connective tissue disorders which have occurred as the result of a deficiency in which the regenerative tissues of the skin and organs lack the ability to produce collagen in sufficient quantities to eradicate the existing disease state. Regeneration is the growth and differentiation of new cells and intercellular substances to form new tissues or parts. It consists of fibroplasia, endothelial proliferation, the deposition of interstitial ground substance and collagen, epithelial hyperplasia and the maturation of connective tissue. Bone and cementum are not replaced by existing bone or cementum, but from connective tissue, which is the precursor of both. Undifferentiated connective tissue cells develop into osteoblasts and cementoblasts which form bone and cementum. In periodontal tissues, regeneration is a microscopic activity which differs in degrees from clinically radiographically detectable restoration of destroyed periodontal tissues. Regeneration in most instances restores the continuity of diseased marginal gingiva and reestablishes a normal gingival sulcus at the same level on the root as the base of the pre-existing periodontal pocket. Reattachment is the re-embedding of new periodontal ligament fibers into new cementum and the attachment of gingival epithelium to tooth surface previously denuded by disease.

The present invention provides the use of misoprostal to produce new epithelium, bone, connective tissue, cartilage, fascia, ligaments, tendons and collagen tissues of type I, II, and III. The use of topical preparations of misoprostol cause an increase in fibroblastic activity in skin and mucous membranes. This results in the production of collagen type I. This can be measured quantitatively. The increased response to healing as a result of this treatment will result in thickening to the skin, lessening of the prominence of facial rhytids, improved skin turgor and elastic properties, accelerated healing of wounds and/or scars resulting from thermal, chemical, or mechanical etiologies, free graft (split or full thickness) survival enhancement, and increased healing of mucous membrane injuries with a decrease in pain associated with all of these conditions as a result of decreased inflammation, coupled with accelerated healing.

In summary, the method of the present invention provides a new treatment that accelerates healing for the patient, reduces trauma from surgeries that no longer need to be performed, and reduces cost to the patient. Also, in necessary surgeries such as gingival grafting, it accelerates healing of both the donor site and graft site. Using misoprostol with a local anesthetic such as dyclonine makes the surgical procedures almost painless. Also, a reduction of dry sockets after extractions is being found with the present procedure, thus almost eliminating them as a problem in the dental office. The advantage for the periodontal patient is that it eliminates much of the surgery if this process is used on early periodontal cases along with good oral hygiene and maintenance care.

The therapy disclosed herein using misoprostol as a topical application has shown dramatic results within as little as 3 to 5 days. Re-epithelialization occurs rapidly with the use of misoprostol when secondary infection is controlled. The usual course of treatment if signs of secondary infection occur is to dose with antibiotic and/or antifungals, in addition to misoprostol topically applied directly to the area.

The effect of chemotherapy and radiotherapy are similar. It is based on the ability to non-specifically destroy or retard the division of rapidly proliferating malignant cells with specific drugs or radiation. Normal cells with rapid turnover, such as oral mucosa or the alimentary canal, are also affected and may result in toxicity and complications. Approximately 20% of patients with cancer are treated with chemotherapy at some time during the course of their disease; also there are approximately 250,000 episodes of oral complications each year. These incidences are likely to increase with the use of more potent drugs and multimodality therapy combining radiation and new chemotherapy.

Control of secondary infections using antibiotics and/or antifungal agents in combination with the present misoprostol routine creates re-epithelialization and inflammation reduction within 3 to 5 days. The application is directly to the injured tissue by gels, ointments, creams or lotions with misoprostol as the active ingredient, preferably 4 to 5 times daily.

Misoprostol is an analog of prostaglandin $E_1$ and is broken down by most tissues of the body to misoprostol acid, the active metabolyte. Misoprostol has been used in the past on a prescription basis as a gastric mucosa protectant and antiulcer agent. Its primary use is the prevention of nonsteroidal anti-inflammatory drug-induced gastric ulcers, and short term treatment of duodenal ulcers. In contrast, the present method demonstrates regeneration or a re-epithelialization of damaged tissues and reduced healing times.

Misoprostol may be administered alone or in combination with other pharmaceutically acceptable agents. Dosages of from not less than about 1 µg per day to no more than about 5 mg per day of the individual compounds per se, or in combinations, are generally effective. In this regard, misoprostol is present in a composition in an amount from about 1 µg to about 1 mg per gram of the composition. Various formulations for the compositions are provided herein. Such formulations may include gels, creams, lotions, ointments, and the like. The compositions and/or formulations may also include additional active ingredients if desired, such as local anesthetics.

The method disclosed herein provides a novel method for the regeneration of collagen-containing tissues. For example, epithelium, bone, connective tissue, cartilage, fascia, ligaments, tendons and other collagen tissues of type I, II or III that have collagen as an organic constituent may all be treated with misoprostol. It will be evident that the method will find ready application for the prevention or treatment of damaged tissues other than those named, for example dermatological tissues, in which faster wound healing is desired. For example, the treatment in the present invention may also find ready application in severe burn and skin regeneration, skin grafts, pressure sores, diabetic ulcers, fissures, post surgery scar reduction, dry socket, ulcerative colitis, rectal and anal fissures. This treatment also improves healing from dermatological surgery, and any surgery involving epithelial tissue.

The present method has the distinct unexpected advantage that it will provide a highly effective treatment for regenerating, not merely preserving or protecting, collagen-containing tissues, and all epithelial tissues, and at the same time this compound advantageously will not produce unwanted systemic or local side effects even if the compound is administered continuously on a daily basis, as long as the appropriate compound dosages are used. It, of course, must be understood that the dosage levels will be adjusted dependent on the response of the subject and the degree of damage to the tissues as monitored by methods known to those skilled in the art.

DETAILED DESCRIPTION OF THE INVENTION

It has now been found that an effective method of regenerating new collagen-containing tissues, especially bone, connective tissue, cartilage, fascia, ligaments, tendons and other collagen-containing tissues of type I, II or III that have a collagen as an organic constituent and epithelium, can be achieved with compositions which include an effective amount of misoprostol.

Misoprostol is an analog of prostaglandin $E_1$ in which the carbon 15 hydroxyl group has been removed and replaced by a hydrogen atom, and the two hydrogen atoms at the carbon 16 position have been removed and replaced by a methyl group and a hydroxyl group. Misoprostol may exist in either the 16R- or 16S- stereoisomeric forms. Structurally, these analogs are characterized by the general formula I or II shown below:

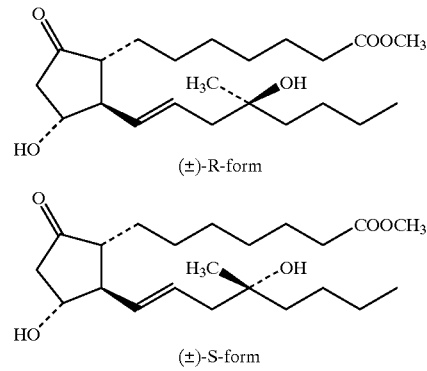

The present method of regenerating human tissues, comprises topically administering to a subject at the site of the tissue a composition having an effective amount of misoprostol. Topical application involves administering an effective daily dose of misoprostol in an amount of from about 1 µg to about 1 mg per gram of the composition which effectively administers 1 µg to about 5 mg misoprostol per day for a desired period, i.e., typically at least four days. The preferred dosage range is dependent upon the particular collagen-containing tissue being treated and the response of the patient to treatment, as is well known by those skilled in the art. For example, preferred ranges for the treatment of tissues, such as wrinkles, might be 4 µg per day to about 800 µg per day while the preferred ranges for the regeneration of tissue necessary because of radiation therapy and/or chemotherapy might be about 4 µg per day to about 1 mg per day.

Misoprostol used in the method of this invention may be synthesized in accordance with known procedures. Accordingly, a description of a method for the preparation of misoprostol is deemed unnecessary herein.

Compositions for use in the above-mentioned treatment of collagen-containing tissues comprise an effective amount of misoprostol as the active ingredient and a suitable carrier. As previously noted herein, an effective amount of misoprostol for use in accordance with this invention is from about 1 µg to about 1mg per gram of composition. A concentration of about 240 µg per gram of composition is preferred. In powder form, the composition contains about 0.004% to about 0.1% misoprostol.

The topical compositions of this invention are formulated preferably as gels, creams, lotions, ointments, time release liposomes and the like by choice of appropriate carriers. Suitable carriers include vegetable or mineral oils, white petrolatum (white soft paraffin), branched chain fats or oils, animal fats and alcohols such as absolute ethanol. The preferred carriers are those in which the active ingredient is soluble. Emulsifiers, stabilizers and anti-oxidants may also be included as well as agents imparting color or fragrance if desired.

Gels containing misoprostol may be formulated by any method known. In one preferred method, a 400 mcg/ml misoprostol gel is made by first dispersing 4 mg of misoprostol in 10 ml of absolute ethanol. The mixture is gelled by adding 0.2 gram of hydroxypropyl cellulose 1500 cps and mixed well. The resultant gel may then be dispensed in 1 ml syringes. Typically, a patient would be instructed to apply 0.3 ml to the treatment site, e.g., the face, four times daily.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, 20 parts beeswax, 39 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil, and about 70% white soft paraffin by weight.

Lotions may be conveniently prepared by dissolving the active ingredient, in a suitable high molecular weight alcohol such as propylene glycol or polyethylene glycol.

It should be recognized that misoprostol will break down to prostaglandin A if in the presence of water. Thus, creams last approximately only one week because of this stability problem. Therefore, misoprostol is best used in a powder form that can be hydrated at the time of use. Misoprostol is more stable in a vehicle that uses propylene glycol. It can be stored in a dry state for a couple years if it is stabilized with hydroxypropyl methyl cellulose. In liquid form as the oil, it is preferably dissolved in absolute alcohol (ethanol) and frozen. The frozen alcohol and misoprostol mixture is stable for at least a year.

One or more additional substances which have therapeutic effects on the skin and/or tissue being treated may also be incorporated in the composition. For example, other suitable types of active ingredients may be incorporated in the compositions of this invention and may include other compounds known to have beneficial effect on skin and/or collagen-containing tissue. Additionally, anti-inflammatory agents as well as local anesthetics such as dyclonine in an amount of about 0.5 to 1% by weight.

The proportions of the misoprostol compound, or each of the compounds in the composition, are dependent upon the particular tissue being addressed and the degree of response desired. Amounts in excess of about 5 mg per day of misoprostol or the combination of that compound with other pharmaceutically acceptable compounds, are generally unnecessary to achieve the desired results, and may not be economically sound practice. In practice the higher doses are used where therapeutic treatment of the tissue is the desired end, while the lower doses are generally used for prophylactic or maintenance purposes; it being understood that the specific dosage administered in any given case will be adjusted in accordance with the specific compounds being administered, the tissue to be treated, the condition of the subject and other relevant medical facts that may modify the activity of misoprostol or the response to the subject, as is well known by those skilled in the art. In general, either a single daily dose or divided daily dosages may be employed, as is well known in the art.

Dosage forms of the compound can be prepared by combining them with a non-toxic pharmaceutically acceptable carrier to make either immediate or slow release formulations as is well known in the art. Such carriers may be either solid or liquid in form such as, for example, cornstarch, lactose, sucrose, peanut oil, olive oil, sesame oil, propylene glycol and water. If a solid carrier is used the dosage forms of the compound of the invention may be powders, troches or lozenges. If a liquid carrier is used, soft gelatin capsules, or syrup liquid suspensions, emulsions or solutions may be the dosage form. The dosage forms may also contain adjuvants, such as preserving, stabilizing, wetting or emulsifying agents, solution promoters, etc. They may also contain other therapeutically valuable substances.

Topical application of compositions containing misoprostol was found to be therapeutically effective in field studies. In a typical example, topical application of a composition containing misoprostol to the tissue four times daily resulted in improved and/or healed tissues. The following examples illustrate the efficacy of compositions containing misoprostol in accordance with the present invention.

EXAMPLE 1

Patient 50 years old was treated with misoprostol gel 400 mcg/ml applied four times per day to lateral border of left eye; right eye applied a placebo. After 45 days, 2 mm punch biopsies were taken from the lateral border of each eye. The tissue was stained with H&E stain and analyzed by a pathologist. The results were an increased thickness of the epithelium and connective tissue of the left biopsy compared to the right side. There was also an increase in the number of fibroblasts on the left side compared to the right side.

EXAMPLE 2

A patient with lateral epicondylitis from work related problems was removed from work and placed on misoprostol gel 400 mcg/ml applied four times per day. Symptoms improved in six weeks and the patient was back to work. Epicondylitis is a ligament and tendon condition resulting in microtears and usually requiring rest of the affected limb for years and almost always requiring surgery.

EXAMPLE 3

A 14 year old patient was examined after surgery on the anterior maxilla and premaxilla from a cyst removal that didn't heal. Bone defect was 2 cm long and 1.5 cm wide on the buccal aspect of the premaxilla in the area of #7 perforated to the palatal and loss of cortical plate 1 cm in diameter. Both areas demonstrated loss of cortical plate and trabecular bone. Critical size of defects in bone renders them to heal as fibrotic tissue rather than normal bone. A flap procedure was performed to expose the defect on the facial surface, fibrotic tissue was removed, the area was flushed with liquid misoprostol, a gortex graft placed of the bone surface to support the soft tissue and the soft tissue sutured for primary closure. The patient used powdered misoprostol four times per day for 7 weeks. The area was reopened to remove the gortex graft. Subsequent x-rays confirm the density of bone compared to preop films and films to date demonstrate that the bone density stays consistent.

EXAMPLE 4

Patient 47 years old presented with severe facial wrinkling. Misoprostol gel 400 mcg/ml was applied four times per day to the face for 45 days four times per day. Punch biopsies 2 mm wide were taken lateral to the corners of the eyes and behind the left ear as a control. The biopsies were stained with H&E stain and analyzed by a pathologist and a researcher specializing in collagen. The facial biopsies demonstrated thicker epithelium and connective tissue. The facial tissue had a dramatic increase in the quantity of fibroblasts compared to the control tissue. Clinical changes were noted pre and post misoprostol, demonstrating that there was almost a complete eradication of the facial wrinkles.

EXAMPLE 5

Patient was a 49 year old male. In collaboration with a dermatologist it was determined to test regrowth of epidermal and dermal tissue of the inferior area of the forearm. Three separate sites approximately 2×4 cm were removed to the capillary dermis by the use of a laser. Site "A" was treated with eucerin cream, site "B" with misoprostol 0.024% in aquaphor and site "C" with misoprostol 0.01% in aquaphor. All treatments were applied four times daily and were to be run for 21 days. The test was terminated after 10 days when site "C" was completely re-epithelialized, site "A" had healed 5 mm and site "B" approximately 3 mm. Site "B" had the fastest tissue regrowth of about 3 mm per day but the tissue was fragile and sloughed when the area was cleaned. The dermatologist decided to continue treatments on site "A" and "B" with the misoprostol 0.01% in aquaphor until re-epithelialization was completed, which was 21 days (11 additional days) for both sites.

We claim:

1. A method of regenerating new collagen-containing human tissue comprising topically administering to collagen-containing human tissue in need of regeneration a composition having an amount of misoprostol effective to provide said regeneration.

2. The method of claim 1 wherein said collagen-containing human tissue in need of regeneration is selected from the group consisting of skin, bone, connective tissue, cartilage, fascia, ligaments, tendons and other collagen-containing tissues of type I, II and III that have collagen as an organic constituent.

3. The method of claim 1 wherein said effective amount comprises from about 1 $\mu$g to about 1 mg misoprostol per gram of composition.

4. The method of claim 1 wherein said composition is a powder mixture which hydrates upon application to form an adhesive gel.

5. The method of claim 4 wherein said powder mixture contains from about 0.004% to about 0.1% misoprostol.

6. A method for regenerating wrinkled human skin comprising topically administering to wrinkled human skin in need of regeneration, an amount of misoprostol effective to provide said regeneration.

* * * * *